US 11,622,496 B2

(12) United States Patent
Kowalchuk

(10) Patent No.: US 11,622,496 B2
(45) Date of Patent: Apr. 11, 2023

(54) SMART SENSOR SYSTEM FOR AGRICULTURAL IMPLEMENTS

(71) Applicant: CNH Industrial Canada, Ltd., Saskatoon (CA)

(72) Inventor: Trevor Lawrence Kowalchuk, Saskatoon (CA)

(73) Assignee: CNH INDUSTRIAL CANADA, LTD., Saskatoon (CA)

( * ) Notice: Subject to any disclaimer, the term of this patent is extended or adjusted under 35 U.S.C. 154(b) by 267 days.

(21) Appl. No.: 16/450,081

(22) Filed: Jun. 24, 2019

(65) Prior Publication Data

US 2020/0396889 A1   Dec. 24, 2020

(51) Int. Cl.
| A01C 5/06 | (2006.01) |
| A01C 7/20 | (2006.01) |
| A01C 7/10 | (2006.01) |
| A01B 47/00 | (2006.01) |
| G01N 33/24 | (2006.01) |

(52) U.S. Cl.
CPC .............. *A01C 5/064* (2013.01); *A01B 47/00* (2013.01); *A01C 7/102* (2013.01); *A01C 7/203* (2013.01); *G01N 2033/245* (2013.01)

(58) Field of Classification Search
CPC ....... A01B 47/00; A01B 79/005; A01C 5/064; A01C 7/102; A01C 7/203
See application file for complete search history.

(56) References Cited

U.S. PATENT DOCUMENTS

| 7,743,844 | B2 | 6/2010 | Kovach et al. |
| 8,418,636 | B2 | 4/2013 | Liu et al. |
| 8,550,020 | B2 * | 10/2013 | Sauder ................. F15B 11/042 |
| | | | 111/200 |
| 8,827,001 | B2 | 9/2014 | Wendte et al. |
| 8,935,986 | B2 | 1/2015 | Blomme et al. |
| 9,282,688 | B2 | 3/2016 | Casper et al. |
| 9,516,802 | B2 | 12/2016 | Zemenchik |
| 9,585,307 | B2 | 3/2017 | Holland |
| 9,629,304 | B2 | 4/2017 | Zielke |
| 9,801,332 | B2 | 10/2017 | Landphair et al. |
| 9,943,027 | B2 | 4/2018 | Sauder et al. |
| 10,123,475 | B2 | 11/2018 | Posselius et al. |
| 2015/0264857 | A1 * | 9/2015 | Achen ................. A01B 63/28 |
| | | | 172/260.5 |
| 2015/0296698 | A1 * | 10/2015 | Schumacher ......... A01B 71/02 |
| | | | 172/4 |
| 2015/0305226 | A1 | 10/2015 | Zemenchik |

(Continued)

FOREIGN PATENT DOCUMENTS

| WO | WO-2012149415 A1 * | 11/2012 | ............. A01C 5/064 |
| WO | WO-2016182906 A1 * | 11/2016 | ......... A01B 63/1112 |

*Primary Examiner* — Thomas B Will
*Assistant Examiner* — Ian A Normile
(74) *Attorney, Agent, or Firm* — Rebecca Henkel; Rickard DeMille

(57) ABSTRACT

An agricultural planting or seeding implement having a ground engaging tool that forms an opening along an axis in the soil, a sensor disposed aft of the ground engaging tool, and a row unit disposed aft of both the ground engaging tool and the sensor relative to a direction of travel of the agricultural planting or seeding implement. The sensor engages with the ground at a depth within the opening and generates a signal indicative of a soil property of the ground.

20 Claims, 4 Drawing Sheets

(56) References Cited

U.S. PATENT DOCUMENTS

| | | |
|---|---|---|
| 2017/0086361 A1* | 3/2017 | Landphair .............. A01C 5/062 |
| 2017/0094889 A1 | 4/2017 | Gamer et al. |
| 2018/0124992 A1 | 5/2018 | Koch et al. |
| 2018/0139891 A1 | 5/2018 | Gerber et al. |
| 2018/0168094 A1 | 6/2018 | Koch et al. |
| 2018/0238823 A1 | 8/2018 | Puhalla et al. |
| 2018/0340845 A1 | 11/2018 | Rhodes et al. |
| 2019/0000004 A1* | 1/2019 | Sloneker ................ A01C 5/064 |
| 2020/0128723 A1* | 4/2020 | Eichhorn ............. A01B 79/005 |
| 2020/0245526 A1* | 8/2020 | Ritland ................ F16K 31/082 |

\* cited by examiner

SMART SENSOR SYSTEM FOR AGRICULTURAL IMPLEMENTS

BACKGROUND

The invention relates generally to agricultural equipment, and more particularly to agricultural planting or seeding implements.

In order to plant a field, seeding implements are typically towed behind a tractor. The seeding implements may include multiple row units distributed across the width of the implement. The row units deposit seeds across the field, creating rows of crops. In order to plant the seeds, the row units typically include a ground engaging tool or opener that forms a trench in the soil for seed deposition below the surface of the field. As the seeding implement traverses the field, the properties of the soil may vary. These properties may include soil moisture, soil temperature, and organic matter content. Unfortunately, the variation in soil properties may affect the emergence and growth of the seeds.

BRIEF DESCRIPTION

Certain embodiments commensurate in scope with the disclosed subject matter are summarized below. These embodiments are not intended to limit the scope of the disclosure, but rather these embodiments are intended only to provide a brief summary of certain disclosed embodiments. Indeed, the present disclosure may encompass a variety of forms that may be similar to or different from the embodiments set forth below.

A first embodiment describes an agricultural planting or seeding implement having a first ground engaging tool that forms an opening along an axis in the soil, a sensor disposed aft of the first ground engaging tool, and a row unit disposed aft of both the first ground engaging tool and the sensor relative to a direction of travel of the agricultural planting or seeding implement. The sensor engages with the ground at a first depth within the opening and generates a signal indicative of a soil property of the ground at the first depth. The row unit includes a second ground engaging tool that forms a trench in the ground at a second depth along the axis, an agricultural product delivery system configured to deliver a first agricultural product into the trench at the second depth, and a depth control system coupled to the ground engaging tool. The depth control system is configured to control the second depth of the trench. A controller coupled to the sensor and the depth control system is configured control the second depth based at least in part on the signal from the sensor.

A second embodiment describes a method of operating a planting or seeding implement. The method includes forming an opening in a ground along an axis with a first ground engaging tool of the agricultural planting or seeding implement, monitoring a soil property at a first depth within the opening with a sensor disposed aft of the first ground engaging tool, and enlarging the opening along the axis to form a trench with a second depth with a second ground engaging tool of the agricultural planting or seeding implement. The sensor is configured to generate a signal indicative of the soil property, and the second ground engaging tool is disposed aft of the sensor. The method includes delivering a first agricultural product into the trench at the second depth, and controlling a depth control system coupled to the ground engaging tool based at least in part on the signal from the sensor. The depth control system is configured to control the second depth.

DRAWINGS

These and other features, aspects, and advantages of the present invention will become better understood when the following detailed description is read with reference to the accompanying drawings in which like characters represent like parts throughout the drawings, wherein.

Figure 3:
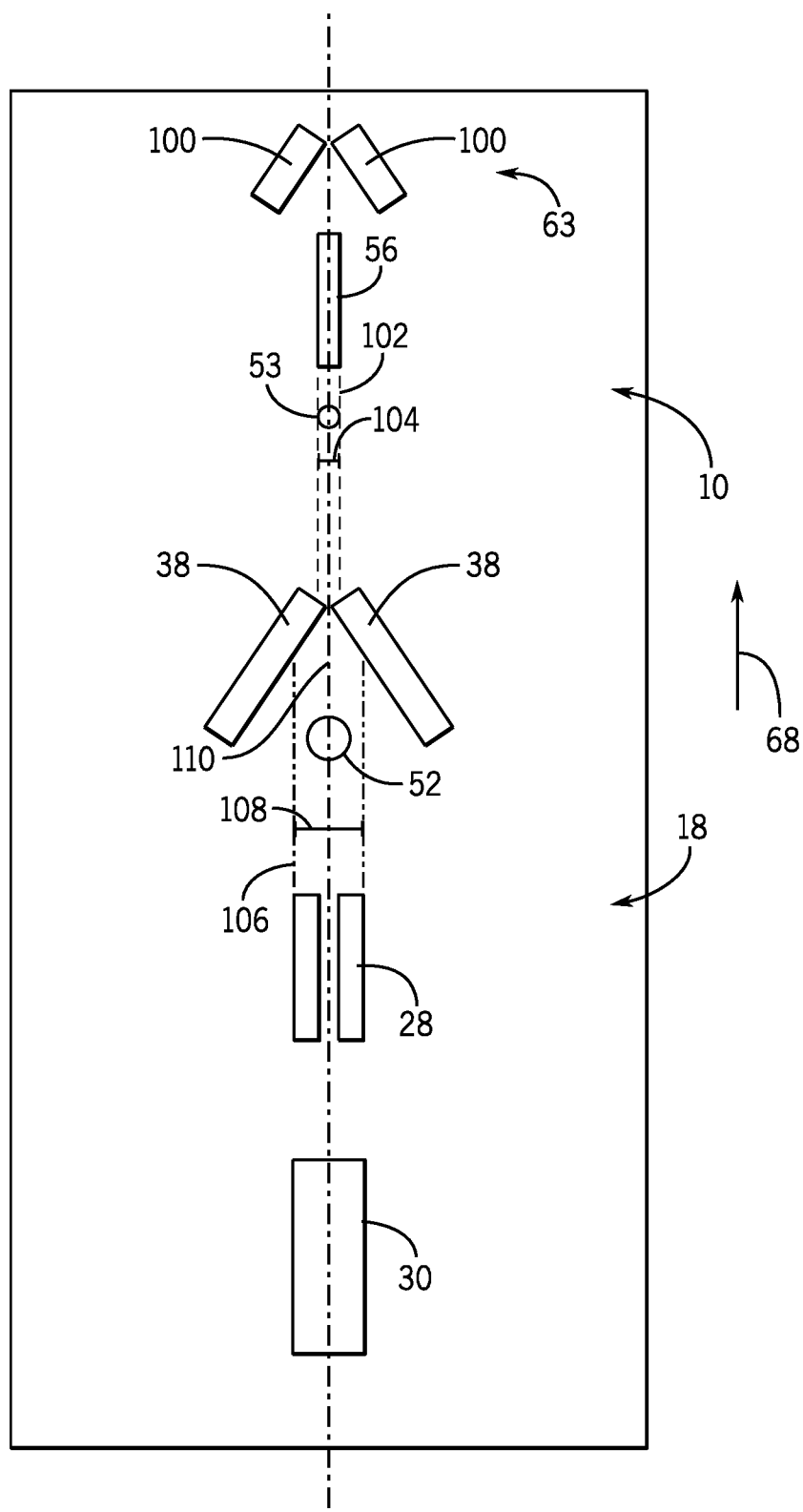
Figure 4:
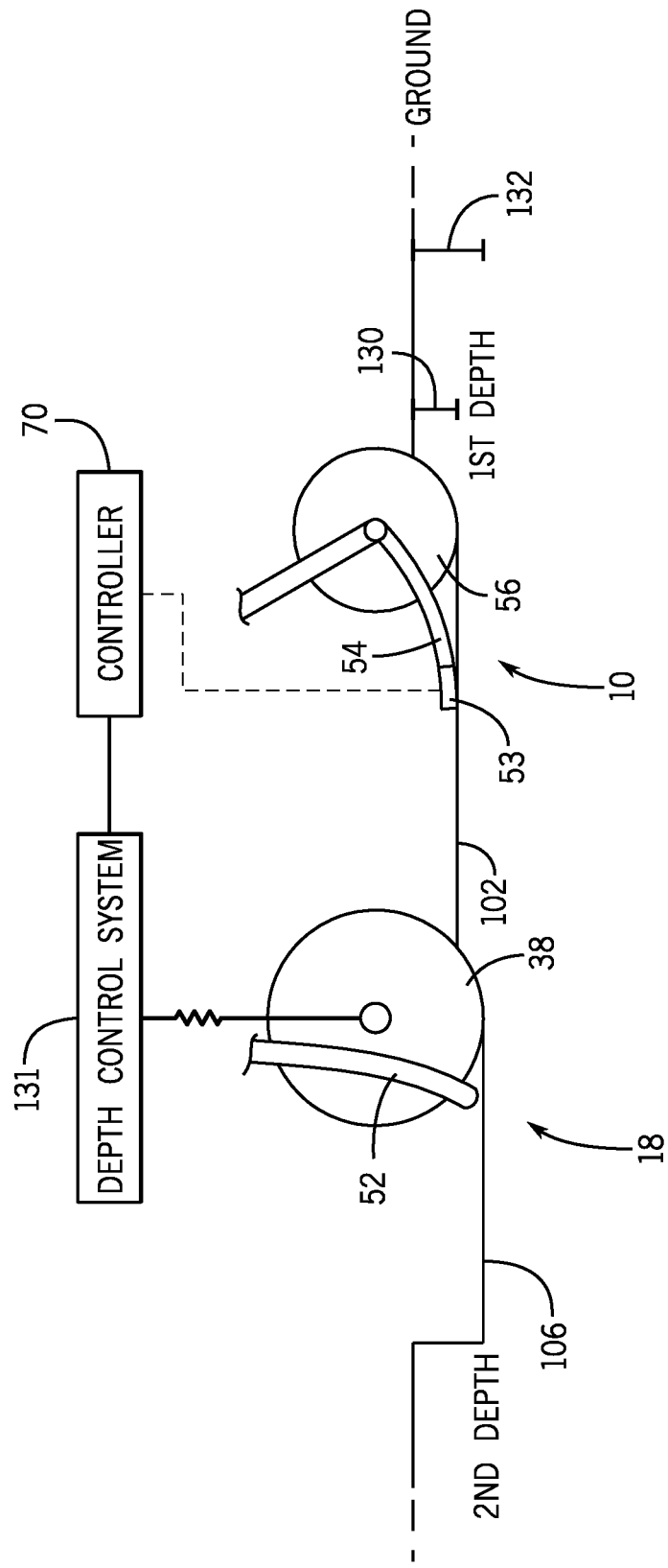

FIG. 3 illustrates a schematic top view of a row unit aft of a soil sensor system in a direction of travel, according to an embodiment of the disclosure; and FIG. 4 illustrates a partial schematic view of an embodiment of a row unit and a soil sensor system with a sensor at a first depth relative to the soil surface and a ground engaging tool at a second depth, according to an embodiment of the disclosure.

DETAILED DESCRIPTION

One or more specific embodiments of the present disclosure will be described below. These described embodiments are only exemplary of the present disclosure. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure is generally directed to agricultural implements that deposit agricultural products into the soil (e.g., seeds). The agricultural implement includes a soil sensor system that enables the detection of soil characteristics or properties that affect the growth and emergence of seeds. These soil characteristics or properties may include soil moisture, soil temperature, and organic matter content. The soil sensor senses these soil characteristics or properties and emit signals indicative of these soil characteristics or properties. The soil sensor system uses these signals to determine the soil characteristics or properties and in response varies the depth of the trench in which the agricultural product is deposited. It should be understood that each row unit on the implement may have an associated soil sensor system that enables soil characteristic or property detection in the path of the row unit. The trench depth of each row unit may therefore be adjusted to facilitate placement of agricultural product in desirable soil conditions.

Figure 1:
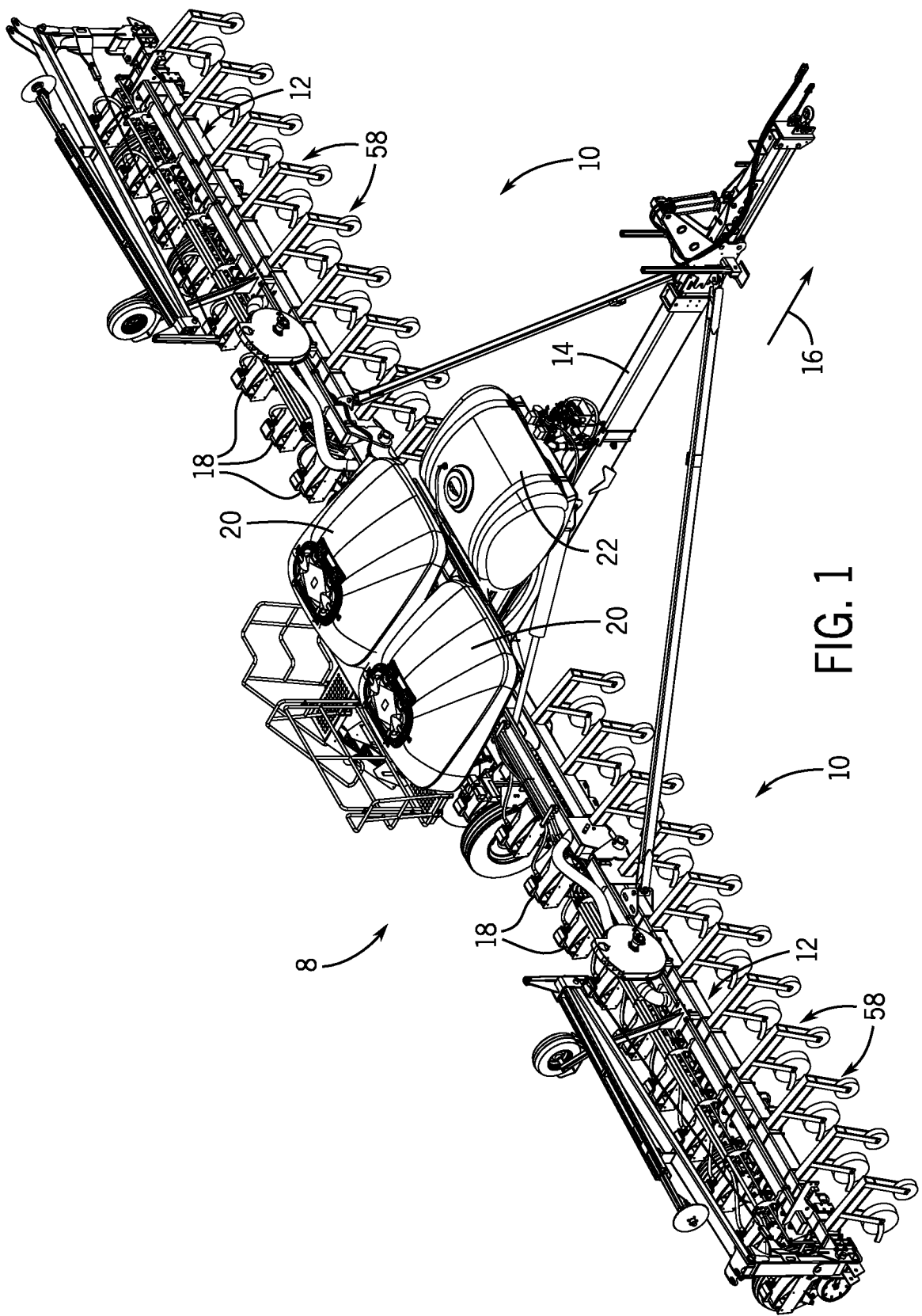
FIG. 1 illustrates a perspective view of an agricultural planting or seeding implement, according to an embodiment of the disclosure.

Referring now to the drawings, FIG. 1 illustrates a perspective view of one embodiment of a planting implement or planter 8 with a soil sensor system 10. As will be explained below the soil sensor system 10 enables detection of soil characteristics or properties. In response to the detected characteristics or properties the planter 8 may adjust the depth at which seeds are planted as the planter 8 traverses the field. It should be understood that the discussion below is equally applicable to a seeding implement, the terms planting and seeding implement should therefore be considered interchangeable.

As shown in FIG. 1, the planter 8 may include a laterally extending toolbar or frame assembly 12 connected at its middle to a forwardly extending tow bar 14 to allow the planter 8 to be towed by a work vehicle (not shown), such as an agricultural tractor, in a direction of travel (e.g., as indicated by arrow 16). The frame assembly 12 may generally be configured to support a plurality of seed planting units (or row units) 18. As is generally understood, each row unit 18 may be configured to deposit seeds at a desired depth beneath the soil surface and at a desired seed spacing as the planter 8 is being towed by the work vehicle, thereby establishing rows of planted seeds. In some embodiments, the bulk of the seeds to be planted may be stored in one or more hoppers or seed tanks 20. Thus, as seeds are planted by the row units 18, a pneumatic distribution system may distribute additional seeds from the seed tanks 20 to the individual row units 18. Additionally, one or more fluid tanks 22 may store agricultural fluids, such as insecticides, herbicides, fungicides, fertilizers, and/or the like. The fluids may be supplied to the individual row units 18 for spraying onto the seeds or soil while planting.

In general, the planter 8 may include any number of row units 18, such as 6, 8, 12, 16, 24, 32, 36, 48, or 61 row units. In addition, it should be appreciated that the lateral spacing between row units 18 may be selected based on the type of crop being planted. For example, the row units 18 may be spaced approximately 30 inches from one another for planting corn, and approximately 15 inches from one another for planting soybeans.

It should also be appreciated that the configuration of the planter 8 described above and shown in FIG. 1 is provided only to place the present subject matter in an exemplary field of use. Thus, it should be appreciated that the present subject matter may be readily adaptable to any manner of planter configuration.

Figure 2:
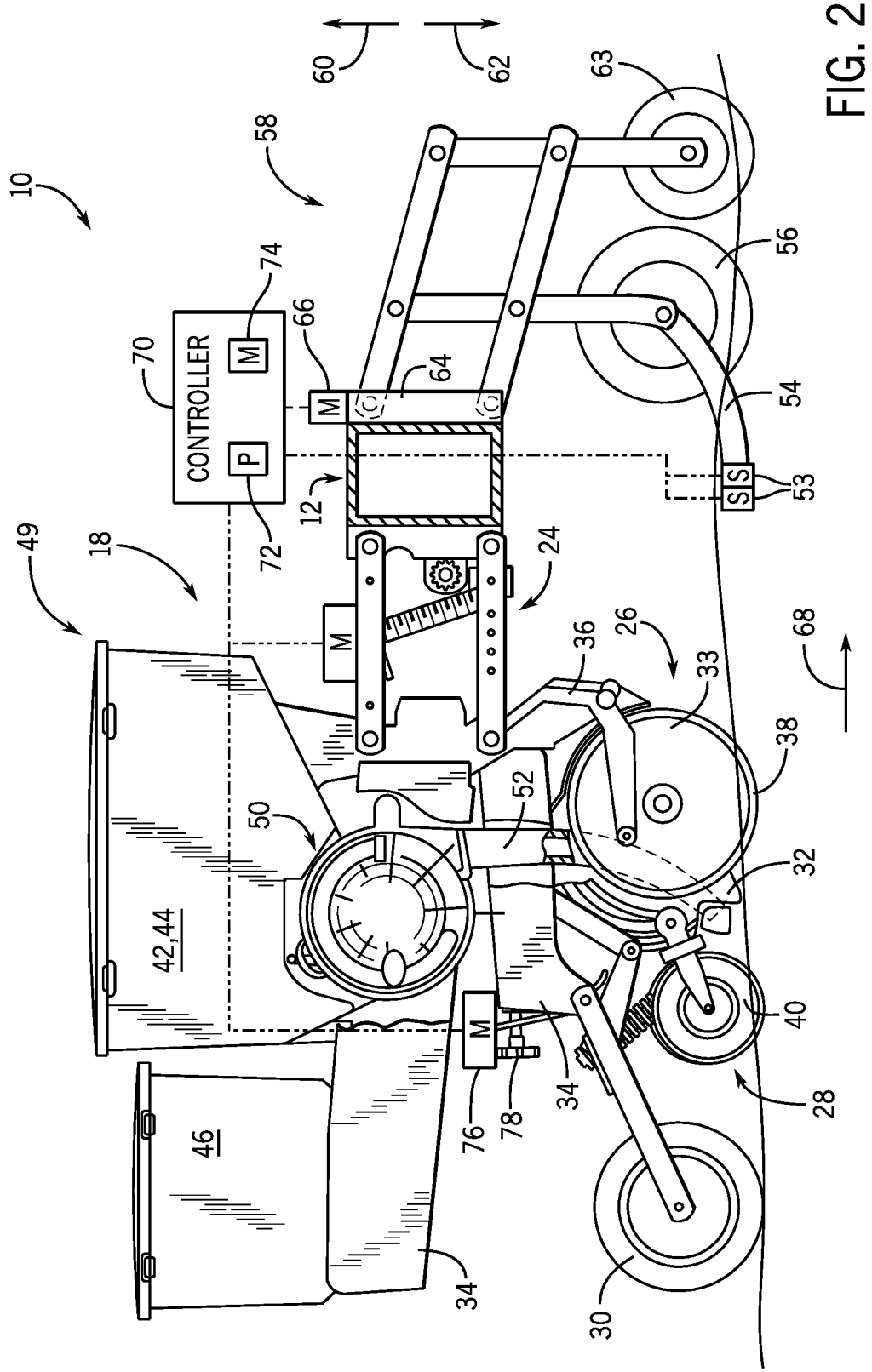
FIG. 2 illustrates a side view of a row unit of an agricultural planting or seeding implement with an agricultural product delivery system aft of a soil sensor system, according to an embodiment of the disclosure.

FIG. 2 is a side view of one embodiment of a soil sensor system 10 and a row unit 18. As shown, the row unit 18 includes a linkage assembly 24 configured to mount the row unit 18 to the toolbar or frame assembly 12 of the planter 8. The row unit 18 also includes a furrow opening assembly 26, a furrow/trench closing assembly 28, and a press wheel 30. In general, the furrow opening assembly 26 may include a gauge wheel 33 operatively connected to a frame 34 of the row unit 18 via a support arm 36. Additionally, the opening assembly 26 may also include one or more opening discs 38 (e.g., coulters) configured to excavate a furrow or trench in the soil and a firming point 32. As is generally understood, the gauge wheel 33 may be configured to engage the surface of the field, with the height of the opening disc(s) 38 being adjusted with respect to the position of the gauge wheel 33 to set the desired depth of the furrow being excavated. Moreover, as shown, the furrow closing assembly 28 may include a closing disc(s) 40 configured to close the furrow after depositing the seeds. The press wheel 30 may then be configured to roll over the closed furrow to firm the soil over the seed and promote favorable seed-to-soil contact.

Additionally, as shown in FIG. 2, the row unit 18 may include one or more seed hoppers 42, 44 and an insecticide hopper 46 supported on the frame 34. In general, the seed hopper(s) 42, 44 may be configured to store seeds received from the seed tanks 20, which are to be deposited within the furrow as the row unit 18 moves over and across the field. For instance, in several embodiments, the row unit 18 may include a first seed hopper 42 configured to store seeds of a first seed type and a second hopper 44 configured to store seeds of a second seed type. However, both seed hoppers 42, 44 may be configured to store the same type of seeds.

Moreover, in accordance with aspects of the present subject matter, the row unit 18 may include a seed meter 50 provided in operative association with the seed hopper(s) 42, 44. In general, the seed meter 50 may be configured to uniformly release seeds received from the seed hopper(s) 42, 44 for deposit within the furrow. For instance, in one embodiment, the seed meter 50 may be coupled to a suitable vacuum source (e.g., a blower powered by a motor and associated tubing or hoses) configured to generate a vacuum or negative pressure that attaches the seeds to a rotating seed disc of the seed meter 50, which controls the rate at which the seeds are output from the seed meter 50 to an associated seed tube 52. As shown in FIG. 2, the seed tube 52 may extend vertically from the seed meter 50 toward the ground to facilitate delivery of the seeds output from the seed meter 50 to the furrow.

As mentioned above, the soil sensor system 10 enables detection of soil characteristics or properties. The soil sensor system 10 may therefore include one or more sensors 53 (e.g., 1, 2, 3, 4, 5) that measure characteristics or properties of the soil. In some embodiments, the sensors 53 may be vertically offset in order to measure characteristics of the soil at different depths. For example, the sensors 53 may measure soil moisture, soil temperature, organic matter content, among others at different soil depths enabling seeds to be deposited at desired depths across a field. In some embodiments, the sensors 53 may include light emitters and detectors. In operation, the light emitters may emit light at one or more wavelengths, depending on characteristic(s) being measured, which is then detected by the detector of the sensor. The changes in the reflected light enable the soil sensor system 10 to determine soil properties and characteristics.

In order to detect the soil characteristics, the sensor(s) 53 are placed below the surface of the soil at a desired depth. The sensors 53 couple to a bar 54 that supports the sensors 53 in a trench or opening in the ground formed by one or more openers 56 (e.g., coulters). Accordingly, as the planter 8 traverses the field, the opener 56 forms a trench that enables the placement of the sensors 53 below the surface of the field. In some embodiments, the bar 54 may couple to the opener 56 (e.g., a bearing that supports the opener 56), or the bar 54 may couple to a linkage assembly 58. For example, the linkage assembly 58 may be a four-bar linkage that mounts to the toolbar or frame assembly 12 of the planter 8. In operation, the linkage assembly 58 enables the opener 56 and bar 54 to be lifted and lowered in directions 60 and 62. In some embodiments, additional tools or equipment may couple to the linkage assembly 58, such as a residue manager 63. By the lifting and lowering the opener 56 and bar 54, the sensors 53 may be placed at a desired depth to measure soil properties. In addition, the lifting of the soil sensor system 10 enables transportation of the planter 8 to and from work sites. In some embodiments, the position of the linkage assembly 58 is controlled with an actuator 64 (e.g., lift system) that includes a motor 66. In other embodiments, the actuator 64 may be a manual actuator or a combination of a manual actuator and an automated actuator (e.g., an actuator powered with a motor).

At a job site, the linkage assembly 58 is lowered enabling the opener 56 to penetrate the soil. As a tractor or other vehicle moves the implement 8 in a direction of travel 68, the opener 56 cuts or otherwise forms a trench in the soil that receives the sensors 53. As the sensors 53 travel along the trench they generate signals indicative of soil properties. These signals are transmitted to a controller 70, which determines the soil characteristics or properties.

The controller 70 may include a processor 72 and a memory 74 used in processing one or more signals from one or more sensors 53. For example, the processor 72 may be a microprocessor that executes software in response to one or more signals from the sensors 53. The processor 72 may include multiple microprocessors, one or more "general-purpose" microprocessors, one or more special-purpose microprocessors, and/or one or more application specific integrated circuits (ASICs), field-programmable gate arrays (FPGAs), or some combination thereof. For example, the processor 72 may include one or more reduced instruction set (RISC) processors.

The memory 74 may include a volatile memory, such as random access memory (RAM), and/or a nonvolatile memory, such as read-only memory (ROM). The memory 74 may store a variety of information and may be used for various purposes. For example, the memory 74 may store processor executable instructions, such as firmware or software, for the processor 72 to execute. The memory may include ROM, flash memory, a hard drive, or any other suitable optical, magnetic, or solid-state storage medium, or a combination thereof. The memory may store data, instructions, and any other suitable data.

As the controller 70 receives signals from the sensors 53, the controller 70 controls operation of the row unit 18. The signals emitted by the sensors 53 are indicative of various soil properties, including soil moisture, soil temperature, and organic matter content. In response, to detecting the soil properties from the sensor signals, the controller 70 controls the motor 76. The motor 76 in turn controls the actuator 78 (e.g., worm gear actuator). The actuator 78 controls movement of the support arm(s) 36 to lift and lower the gauge wheel 33 in directions 60 and 62. For example, in response to detection by the controller 70 of soil moisture below a threshold level, the controller 70 may signal the motor 76 to lower the discs 38 into the soil, with the actuator 78, enabling the formation of a deeper trench. A deeper trench may place the seeds in more moist soil. As the planter 8 traverses the field, the moisture content of the soil may increase. As the controller 70 detects the increase in soil moisture through communication with the sensors 53, the controller 70 may determine that the moisture content is greater than a threshold level. In response to the increased soil moisture, the controller 70 may signal the motor 76 to lift the linkage assembly 24 with the actuator 78 to reduce the depth of the trench. In this way, the controller 70 may lift or lower the discs 38 in response to signals from the sensors 53. It should be understood that the lifting and lowering the discs 38 may also be in response to other soil properties (e.g., soil temperature, and organic matter content) that are less than or greater than a threshold level.

In some embodiments, the controller 70 may receive feedback from multiple sensors 53 each providing feedback regarding one or more soil properties. However, the measured levels and/or amounts of these properties may not all be within desired threshold levels. For example, a first property may be below a threshold amount while a second property is greater than a threshold level. In these situations, the controller 70 may be programmed to provide a solution that favors one property (e.g., soil moisture) over another property (e.g., soil temperature). That is, the controller 70 may increase or decrease the depth of the trench to increase one soil property over another soil property. In another embodiment, the controller 70 may be programmed to find a depth solution that compromises between the two properties. For example, the depth of the trench may not optimize soil moisture and organic matter content but improves both properties or improves both properties but does not improve a first property as much as the second property. It should be understood that the controller 70 may be programmed to adjust the depth in response to multiple soil property conditions (e.g., 1, 2, 3, 4, 5) that are sensed by one or more sensors 53.

As illustrated, the sensors 53 are in front of the discs 38 and the seed tube 52 in the direction of travel 68. In this position, the controller 70 is able to receive and process signals from the sensors 53 before the discs 38 and seed tube 52 reach the same location. The controller 70 is therefore able to adjust the depth of the trench by lifting or lowering the row unit 18 with the motor 76 and actuator 78 before reaching the previous position of the sensors 53. The seeds may therefore be planted at a desired depth in response to the sensor signals indicative of one or more soil properties.

In some embodiments, the controller 70 may also control movement of the linkage assembly 58 to control the depth at which the sensors 53 detect soil properties. In other words, the controller 70 controls movement of the linkage assembly 58 to control the depth at which the opener 56 penetrates the soil and creates the trench that the sensors 53 ride in. For example, as the controller 70 receives signals from the sensors 53, the controller 70 controls the depth of the trench in order to determine how soil properties vary with depth. The controller 70 controls the depth of the trench by controlling the motor 66. The motor 66 in turn controls the actuator 64 (e.g., worm gear actuator) to control movement of the linkage assembly 58 in directions 60 and 62.

FIG. 3 illustrates a schematic top view of a row unit 18 and the soil sensor system 10. The row unit 18 and soil sensor system 10 move in direction 68 as the implement 8 is towed across a field. As explained above, a residue manager 63 may be first in the direction of travel 68. As the residue is pulled across the field, the residue manager 63 cuts plant residue and/or mounds of soil in the way of the row unit 18. The residue manager 63 may include one or more discs 100. Behind the residue manager 63 is the opener 56. The opener 56 creates a trench 102. The opener 56 may be a disc(s), knife, shank, or another type of opener that creates the trench 102. As illustrated, the trench 102 defines a width 104. Following the opener 56 are one or more sensors 53 that emit signals indicative of soil properties. As explained above, the controller 70 (seen in FIG. 2) receives these signals and in response adjusts the depth of the disc 38 that cuts a trench 106. It is into this trench that the seeds and/or fertilizer are deposited through the tube 52. As illustrated, the trench 106 may define a width 108 that is greater than the trench 102 formed by the opener 56. The increased width of the trench 108 may enable sufficient seeds and/or fertilizer to be placed in the trench 106 at the desired depth. In some embodiments, the seed tube 52 and sensors 53 are centered on an axis 110. By centering the seed tube 52 and the sensors 53 the accuracy of seed placement in the desired soil conditions may increase. After depositing the seeds and/or fertilizer the trench closing assembly 28 pushes soil into the trench, which is then pressed with the press wheel 30.

FIG. 4 is a partial schematic view of the row unit 18 and the soil sensor system 10. As illustrated, the sensors 53 and the discs 38 may be at different depths. For example, the opener 56 may form a trench at a first depth 130 that enables the sensors 53 to measure soil properties at the first depth. In response, to signals from the sensors 53, the controller 70 may determine that the desired seed placement depth is different than the first depth. For example, if the controller 70 determines that the soil moisture and/or temperature is respectively low and high, the controller 70 may adjust the position of the discs 38 with the depth control system 131 (e.g., actuator 78 and motor 76) to increase the depth of the trench for placement of the seeds at a second depth 132. In some situations, the controller 70 may decrease the second depth 132 with the depth control system 131 so that first depth 130 is greater than or equal to the second depth in response to feedback from the sensors 53. By adjusting the depth of the seeding trench 106 with the depth control system 131, in response to feedback from the sensors 53, the implement 8 may plant each row of seeds in soil conditions that may facilitate growth of the seeds and an associated increase in the crop yield during the harvest.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An agricultural planting or seeding implement, comprising:
    a coulter disc configured to form an opening along an axis in a ground;
    a sensor disposed aft of the coulter disc relative to a direction of travel of the agricultural planting or seeding implement, wherein the sensor is configured to engage with the ground at a first depth within the opening and to generate a signal indicative of a soil property of the ground at the first depth;
    one or more residue tools disposed fore of the coulter disc relative to the direction of travel;
    a row unit disposed aft of the coulter disc and the sensor relative to the direction of travel, wherein the row unit comprises:
        a ground engaging tool configured to form a trench in the ground at a second depth along the axis;
        an agricultural product delivery system configured to deliver a first agricultural product into the trench at the second depth and at a deposit location along the axis; and
        a depth control system configured to control the second depth of the trench; and
    a controller coupled to the sensor and to the depth control system, wherein the controller is configured to control the second depth at the deposit location based at least in part on the signal from the sensor when the sensor was disposed at the deposit location in the opening.

2. The agricultural planting or seeding implement of claim 1, comprising a linkage assembly, wherein the coulter disc, the one or more residue tools, and the sensor are coupled to the linkage assembly, and the linkage assembly enables the coulter disc and the sensor to be lifted and lowered to control the first depth.

3. The agricultural planting or seeding implement of claim 1, wherein the row unit is disposed a first distance aft of the sensor relative to the direction of travel, and the first distance is greater than 12 inches.

4. The agricultural planting or seeding implement of claim 1, wherein the depth control system comprises an actuator, and the controller is configured to control a pneumatic flow to the actuator or a hydraulic flow to the actuator to adjust the second depth.

5. The agricultural planting or seeding implement of claim 1, wherein the controller is configured to control the one or more residue tools based on the signal from the sensor.

6. The agricultural planting or seeding implement of claim 1, wherein the controller is configured to control a rate of delivery of the first agricultural product into the trench based at least in part on the signal from the sensor.

7. The agricultural planting or seeding implement of claim 1, wherein the signal from the sensor is indicative of a temperature of the soil, a residue level of the soil, a moisture of the soil, or any combination thereof.

8. A method, comprising:
    forming an opening in a ground along an axis with a coulter disc of an agricultural planting or seeding implement;
    monitoring a soil property at a first depth within the opening with a sensor disposed aft of the coulter disc, wherein the sensor is configured to generate a signal indicative of the soil property;
    clearing, via one or more residue tools, a residue from the ground fore of the coulter disc;
    enlarging the opening along the axis to form a trench with a ground engaging tool of the agricultural planting or seeding implement, wherein the ground engaging tool is disposed aft of the sensor, and the trench comprises a second depth;
    delivering a first agricultural product into the trench at the second depth and at a deposit location along the axis with an agricultural product delivery system disposed aft of the sensor; and
    controlling a depth control system to control the second depth at the deposit location based at least in part on the signal from the sensor when the sensor was disposed at the deposit location in the opening.

9. The method of claim 8, comprising:
    controlling the one or more residue tools based at least in part on the signal from the sensor, wherein the signal is indicative of a residue level of the soil at the first depth.

10. The method of claim 8, comprising adjusting the second depth of the trench without adjusting the first depth within the opening.

11. The method of claim 8, wherein monitoring the soil property at the first depth within the opening with the sensor comprises engaging the sensor with the ground in the opening at the first depth.

12. The method of claim 8, wherein the soil property comprises a temperature of the soil, a residue level of the soil, a moisture of the soil, or any combination thereof.

13. The method of claim 8, comprising controlling a rate of delivery of the first agricultural product into the trench based at least in part on the signal from the sensor.

14. The method of claim 11, comprising adjusting the first depth of the sensor within the opening independently of the second depth of the trench.

15. The method of claim 8, comprising lifting or lowering the coulter disc and the sensor via a linkage assembly to control the first depth, wherein the coulter disc and the sensor are coupled to the linkage assembly.

16. An agricultural planting or seeding implement, comprising:
    a coulter disc configured to form an opening along an axis in a ground;
    a sensor disposed aft of the coulter disc relative to a direction of travel of the agricultural planting or seeding implement, wherein the sensor is configured to engage with the ground at a first depth within the opening and to generate a signal indicative of a soil property of the ground at the first depth;

one or more residue tools disposed fore of the coulter disc relative to the direction of travel;

a row unit disposed aft of the coulter disc and the sensor relative to the direction of travel, wherein the row unit comprises:

a ground engaging tool configured to form a trench in the ground at a second depth along the axis;

an agricultural product delivery system configured to deliver a first agricultural product into the trench at the second depth and at a deposit location along the axis; and a depth control system configured to control the second depth of the trench; and a controller coupled to the sensor and to the depth control system, wherein the controller is configured to control the second depth at the deposit location based at least in part on the signal from the sensor.

17. The agricultural planting or seeding implement of claim 16, comprising a linkage assembly, wherein the coulter disc, the one or more residue tools, and the sensor are coupled to the linkage assembly, and the linkage assembly enables the coulter disc and the sensor to be lifted and lowered to control the first depth.

18. The agricultural planting or seeding implement of claim 16, wherein the sensor is configured to be centered on the axis, and the agricultural product delivery system is configured to be centered on the axis.

19. The agricultural planting or seeding implement of claim 1, wherein the sensor is configured to be centered on the axis, and the agricultural product delivery system is configured to be centered on the axis.

20. The method of claim 8, wherein the sensor is configured to be centered on the axis, and the agricultural product delivery system is configured to be centered on the axis.

\* \* \* \* \*